United States Patent [19]
Hall et al.

[11] Patent Number: 5,300,096
[45] Date of Patent: Apr. 5, 1994

[54] ELECTROMYOGRAPHIC TREATMENT DEVICE

[76] Inventors: H. Eugene Hall, 10029 NE. 27th St., Bellevue, Wash. 98004; William A. Munday, 6503 57th Ave. NE., Seattle, Wash. 98115; R. Wayne Fields, 6490 Chessington La., Gladstone, Oreg. 97027; James E. Tillman, 1462 38th Ave., Seattle, Wash. 98122

[21] Appl. No.: 892,942

[22] Filed: Jun. 3, 1992

[51] Int. Cl.$^5$ ............................................. A61N 1/18
[52] U.S. Cl. ...................................................... 607/48
[58] Field of Search .................. 128/421, 419 R, 422, 128/423 R, 423 W, 733, 901, 905

[56] References Cited

U.S. PATENT DOCUMENTS

| | | | |
|---|---|---|---|
| 2,465,838 | 3/1949 | Bernard | 128/421 |
| 4,392,496 | 7/1983 | Stanton | 128/423 W |
| 4,582,049 | 4/1986 | Ylvisaker | 128/423 W X |
| 4,690,146 | 9/1987 | Alon | 128/422 |
| 4,811,742 | 3/1989 | Hassel et al. | 128/733 |
| 4,813,418 | 3/1989 | Harris | 128/421 |
| 4,832,033 | 5/1989 | Mather et al. | 128/421 |
| 4,844,075 | 7/1989 | Liss et al. | 128/419 R |
| 4,848,347 | 7/1989 | Hall | 128/420 A |
| 4,863,157 | 9/1989 | Mendel et al. | 272/73 |
| 4,875,484 | 10/1989 | Anzai et al. | 128/421 |
| 4,919,139 | 4/1990 | Brodard | 128/421 |
| 4,919,140 | 4/1990 | Borgens et al. | 128/422 |
| 4,919,148 | 4/1990 | Muccio | 128/798 |
| 5,016,635 | 5/1991 | Graupe | 128/421 |
| 5,070,873 | 12/1991 | Graupe et al. | 128/423 W |

FOREIGN PATENT DOCUMENTS

972199  9/1949  Fed. Rep. of Germany ...... 128/422

Primary Examiner—Lee S. Cohen
Assistant Examiner—Jeffrey R. Jastrazab
Attorney, Agent, or Firm—Michael J. Folise

[57] ABSTRACT

An electrical muscle stimulator converts electromyographic (EMG) signals to digital words for analysis and display by a computer program. The therapist selects a variety of different parameters appropriate for the individual patient, and instructs the device to initiate stimulating signals on command, or upon detection of a suitable EMG signal from the patient. The device that converts digital words representing the selected parameters into complex, bipolar therapeutic pulses. The device can digitally model a wide variety of wave forms and graphically assist the therapist in developing and shaping various wave pulse trains.

16 Claims, 12 Drawing Sheets

ELECTROMYOGRAPHIC TREATMENT DEVICE

GOVERNMENTAL RIGHTS

This invention was made with government support under Small Business Innovation Research Program Grant #5 R44 HD24403-03, awarded by the National Institute of Child Health and Human Development, National Institutes of Health. The government has certain rights in this invention.

TECHNICAL FIELD

The invention relates generally to electrical stimulation of muscles in rehabilitation therapy. Specifically, the invention relates to methods and techniques for applying electrical muscle stimulation in the presence or absence of a natural myographic signal.

BACKGROUND ON THE ART

The application of electrical stimulus to neuromuscular structure for beneficial purposes is well known. Treatment of this type is employed for pain and edema reduction, neuromuscular re-education, and reduction of spasticity.

The electrical and biochemical aspects of muscle contraction are relatively well known, and are described in detail by Benton et al. "Functional Electrical Stimulation—A Practical Clinical Guide", second edition, Ranchos Los Amigos Rehabilitation Engineering Center, Downey, Calif., which is incorporated herein by reference. Electrical muscle stimulation (EMS) has significantly enhanced muscle function in individuals suffering from neurological impairment due to stroke, cerebal palsy, and other conditions which effect the muscular system.

Muscle contraction is a complex electrical-biochemical event which requires transmission of an electrical signal from the brain to the localized nerves within the muscles. If the signal has sufficient amplitude and frequency, a biochemical reaction is established within the nerve fibers generating a series of constructively interfering muscle twitches culminating in a strong contraction. A signal which is inadequate either in electrical amplitude, or frequency does not result in a summating contraction known as "tetanization".

In individuals having healthy nervous systems, electrochemical signals of between 800 to 1000 $\mu V$ can be generated during a strong muscle contraction. In individuals having impaired neuromuscular systems, the initiating signal for strong muscle contraction can be as small as 100 to 250 $\mu V$, substantially below the threshold value necessary for tetanization. These signals can be received and viewed on an electromyogram. This electromyographic (EMG) signal is a complex sinusoid having a frequency of approximately one $kH_z$. This signal can be used to trigger an externally generated therapeutic signal causing the desired muscle to contract when a patient undergoing therapy generates the EMG signal. This is described on pages 17 and 41 by Benton et al. The relationship between applied voltage and time, or current strength and time, respectively is well known for applications employing external electrodes on the surface of the skin. To excite impaired muscle, a signal having a magnitude of 90 V for 10 msec, or 50 V for 300 msec is sufficient. A strong wrist extension can be achieved by applying a current amplitude of 60 mA for 100 $\mu sec$ or 40 mA for a duration of 300 $\mu sec$.

It is now well known that a variety of additional factors influence the therapeutic effect, patient comfort, and safety of EMS therapy. It is well known for example that muscles cannot be continuously stimulated and that an appropriate duty cycle (ratio of time on to time off) of 1:3, to 1:5 is desired. EMS signals are also preferably applied in pulses varying in polarity (i.e. bipolar) with respect to the background electromyographic signal of a patient at rest. Furthermore, the EMS signals should be delivered in a preferred frequency range of 30 to 70 pulses per second. Further yet, patients are most comfortable if the initial pulses are at less full amplitude, and slowly grow to the fully desired amplitude. Still further, pulses of differing shapes (i.e. square wave, exponentially decaying trailing edge, etc) each have their own beneficial purpose. Moreover, the treatment should not apply net direct current to the patient. Thus, even if positive and negative pulses have different wave forms, the areas under each pulse should be equal. Superposition of the above parameters can result in a pulse train 12 in FIG. 2 consisting of a series of individual pulses 14 having varying magnitude so as to establish a leading edge slope or "rise time" 16, a general magnitude of 18, a pulse frequency defined by the pulse period 20, and a total duration defined by the length (in the time domain) 24 of the pulse train 12. As previously stated, the width 24 of each pulse can also vary for different therapeutic effects.

Figure 2:
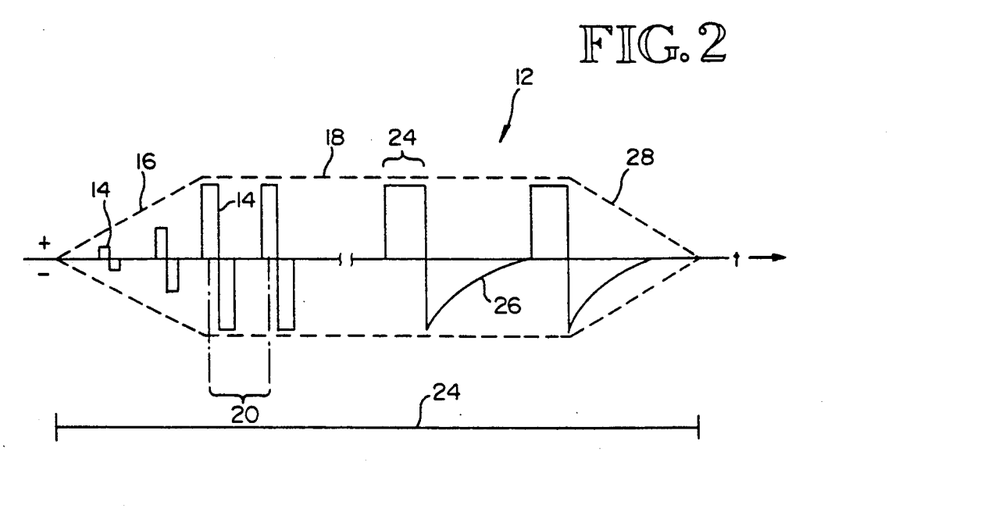
FIG. 2 is a graphic representation of a single pulse train in a stimulation signal.

As shown in FIG. 2, a positive pulse in the form of a square wave may be combined with a negative pulse in the form of an exponentially decaying function 26. Enlarging the pulse width 24 requires an increase in the time constant of the exponential function 26 so that the areas under each curve is equal and a DC charge is not imparted to the patient. The assignee of the present invention has also discovered that the fall time 28 of the pulse train envelope is also significant for patient comfort.

Figure 3:
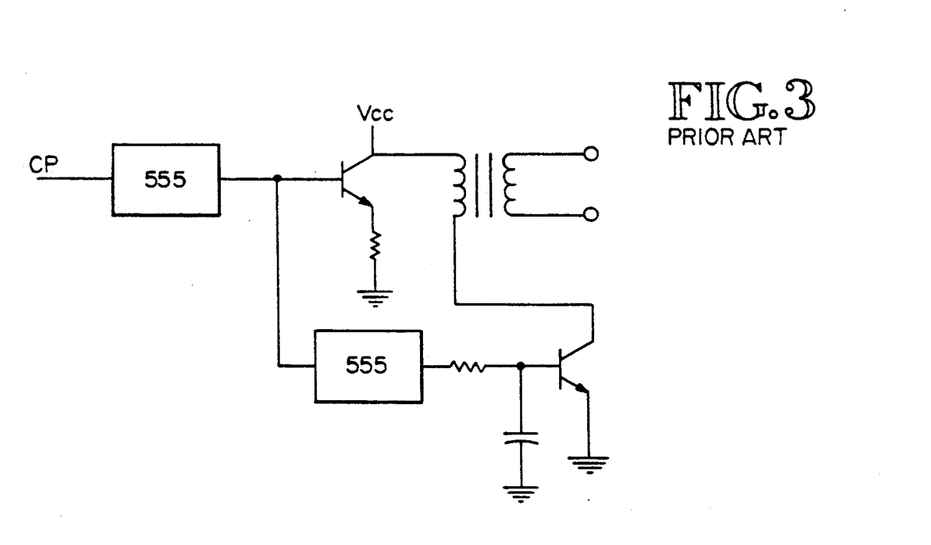
FIG. 3 is an illustration of a prior art circuit for generating bipolar pulses.

It should be appreciated that the therapist operating equipment which generate EMS signals as shown in FIG. 2 is now confronted with a difficult and tedious task in setting up and monitoring the EMS equipment. Furthermore, most prior art devices use electronic circuits employing discrete analogue, and simple digital circuits such as those shown in FIG. 3 which do not facilitate modifications of the parameters discussed above by the therapist. For example, the neuromuscular stimulating apparatus disclosed by Alon, U.S. Pat. No. 4,690,146 employs discrete ramp generators, transition detectors, On-Off timers and the like to control some of the parameters described above. However, the majority of the parameters which make up the pulse trains (the stimulation signal) are not variable. Control of these parameters by the therapist is either unavailable or is by a means of dials and switches. The Dynamic Servostim ™ electromyographic triggered, electrical stimulator (Model 1023) manufactured by Electronic Medical Instruments, Inc., Bellevue, Wash. is typical of the state of the art for multichannel (i.e. capable of stimulating more than one muscle group) systems which provide a rectangular monophasic pulse train, variable amplitude, adjustable pulse rate, and pulse width selectable at either 0.3 msec or 1.0 msec. The initial amplitude of the pulses rises to full amplitude within 0.1 seconds to maximize sharpness of the proprioceptive feedback wave front and is not adjustable. Readouts of these parameters are provided by discrete LEDs, and an LED numeric display. When using both channels to energize complimentary muscle groups in a rhythmic fashion, the set up procedure can be complex and time consuming.

Various prior art devices have attempted to control set up parameters such as: pulse amplitude, pulse duration, pulse recurrence frequency, duration of a pulse train, the time interval separating two consecutive pulse trains, and the slope of the pulse trains under microprocessor control as in U.S. Pat. No. 4,919,139 to Brodard. However, the shape of individual pulses are not controllable and there is no significant enhancement to the therapist's task in establishing the parameters, although they are recorded on EEPROM cards associated with individual patients. Still other devices which employ personal computers, such as Maher et al., U.S. Pat. No. 4,832,033 facilitate preprogramming of individual simulation devices but do not significantly reduce the therapist's tedious and complex task of establishing and monitoring complex stimulation signals prepared for each patient individually.

Therefore, a need exists for an electrical muscle stimulation apparatus which permits instantaneous control of all the applicable parameters which define a stimulation signal, and which assists the therapist in constructing and monitoring the application of such signals.

SUMMARY OF THE INVENTION

It is therefore an object of the present invention to provide an electrical muscle stimulation (EMS) apparatus which permits therapist to vary any one or all of the parameters which define a stimulation signal.

It is another object of the invention to provide an electrical muscle stimulation apparatus which present stimulation signal data in an user friendly manner for evaluation by the therapist.

It is yet another object of the present invention to monitor and display electromyographic (EMG) signals generated by a patient at rest, and when the patient attempts a muscle contraction, in a user friendly manner.

The invention achieves these and other objects and advantages which will become apparent from the description which follows, by employing a computer program in a digital computer to drive a graphic interface between the therapist and sensing/stimulation circuits which are connected to the patient by electrodes. The display graphically illustrates various parameters selectable by the therapist prior to stimulation, as well as EMG data from the patient. The therapist then selects one or all of the relevant parameters for the stimulation signal. The stimulation signal is either triggered by the therapist or by a threshold EMG signal from the patient.

In the preferred embodiment of the invention, the stimulation signals are delivered through the same electrodes from which a patient's EMG data is collected. EMG signals from the patient are conditioned and converted into digital words which are displayed graphically by the computer program on the computer display. The therapist selects various parameters including but not limited to upper and lower (relaxed) EMG threshold values for triggering a stimulation signal, pulse train repetitions, rise time, amplitude, fall time and duration, and pulse cycle frequency. Duty cycle and pulse width can also be selected.

The above data is displayed graphically for each channel prior to initiation of the stimulation for review and modification by the therapist. A sequence of pulse trains can also be previewed graphically. Background signals generated by the patient are automatically nulled. The entire stimulation program for a patient is automatically stored and updated at the end of each session.

BEST MODE FOR CARRYING OUT THE INVENTION

Figure 1:
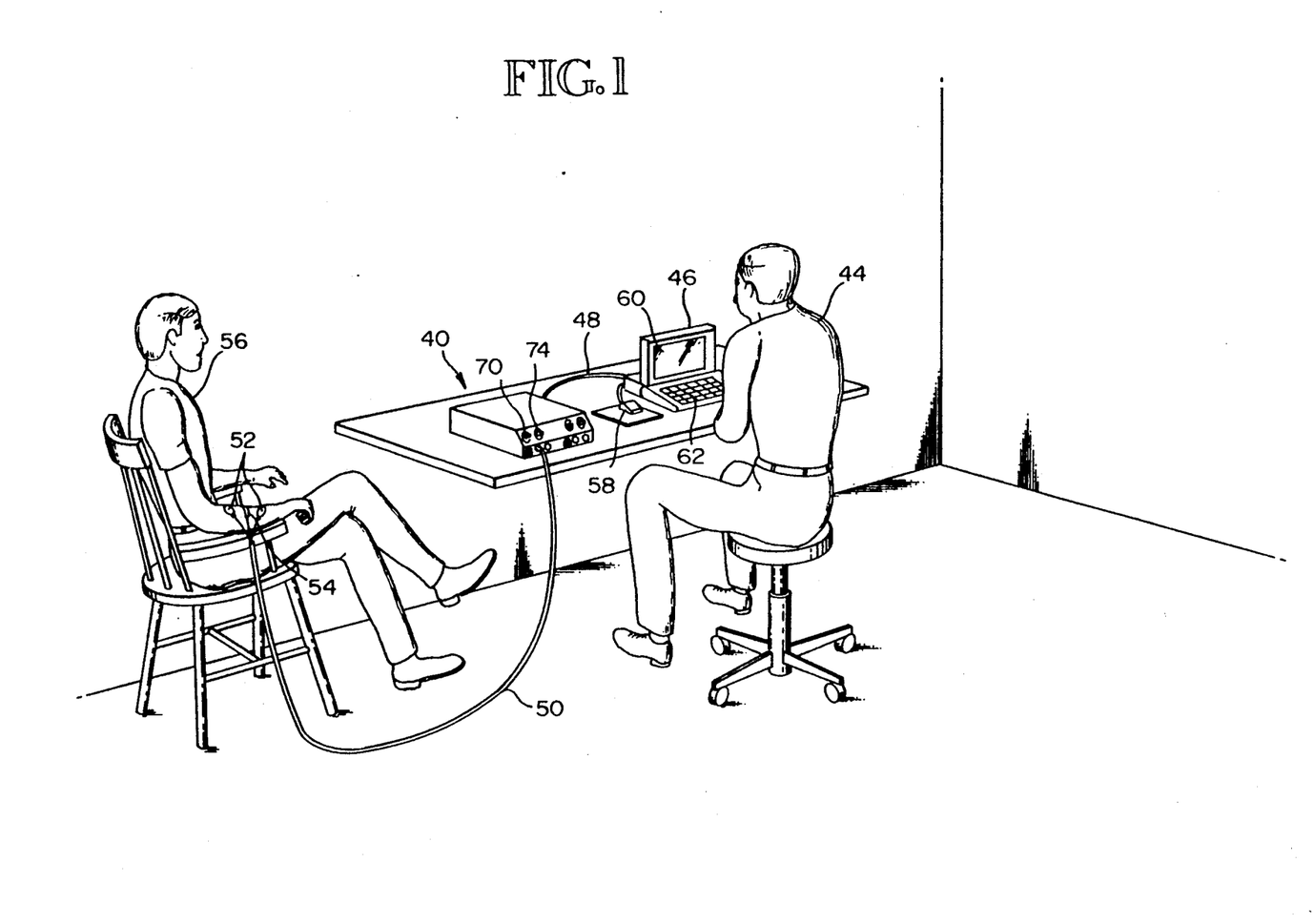
FIG. 1 is an isometric view of a patient undergoing treatment from a therapist using the invention.

An electromyographic stimulator (or electrical muscle stimulator—EMS) in accordance with the principles of the present invention is generally indicated at reference numeral 40 in FIG. 1. The stimulator is controlled by a therapist 44 operating a conventional personal computer 46 which is operatively connected with the stimulator by a cable 48 and personal computer expansion board (not shown). At least one electrode cable 50 having a pair of active electrodes 52 and a reference electrode 54 are attached to the arm of a patient 56. The personal computer preferably employs a pointing device such as a mouse or track ball 58 for facilitating control of software from the computer display 60 by the point and click method. The therapist may of course employ the cursor keys on the computer keyboard 62.

Overview

Figure 4:
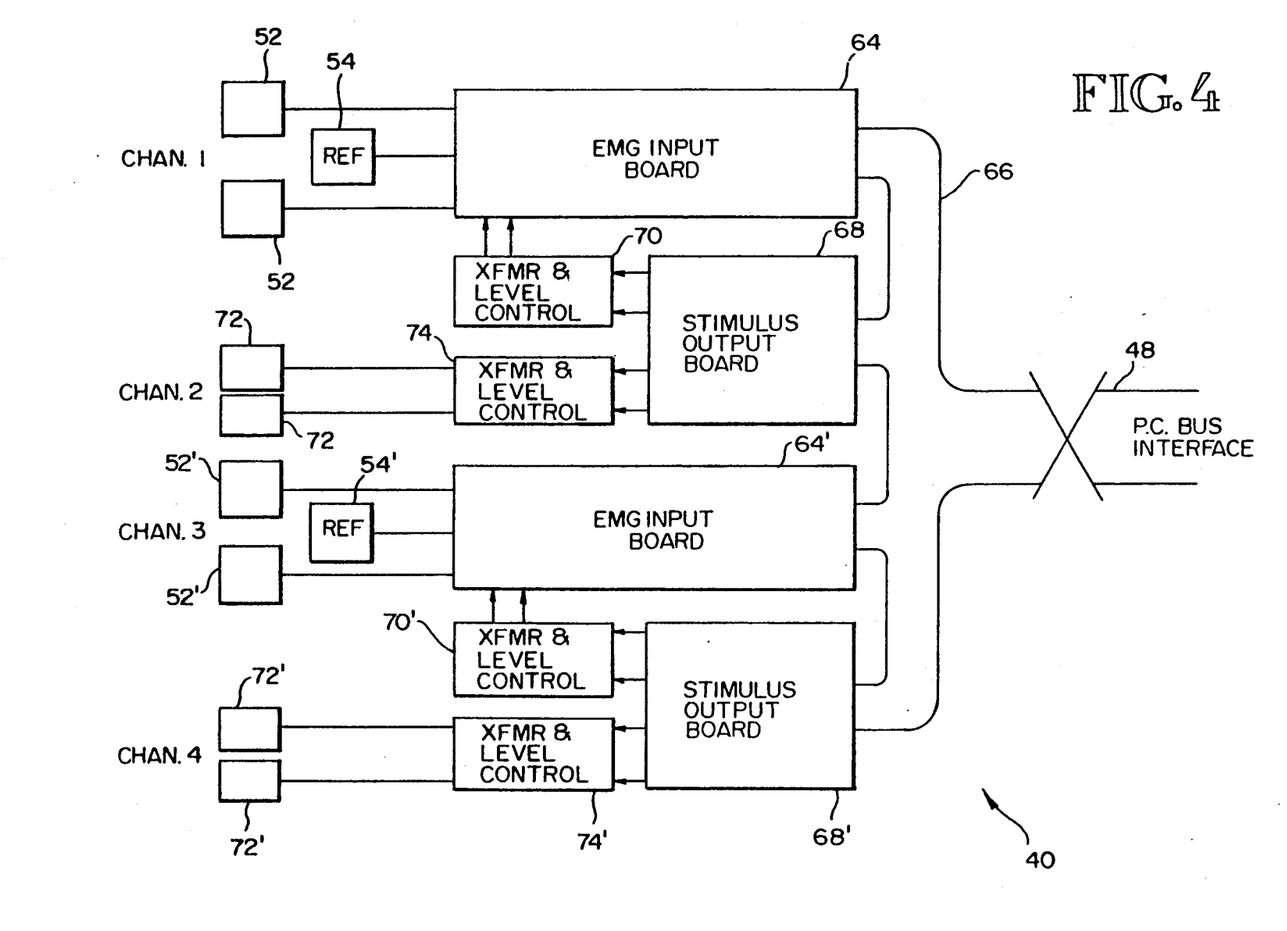
FIG. 4 is a high level block diagram of the present invention.

As shown in FIG. 4, the stimulator 40 has four channels numbered sequentially with the third and fourth channels being mirror images of the first two channels with like reference numerals indicated by a prime symbol. A brief description of the operation of channel one will serve as an introduction to the stimulator 40. In an automatic mode of operation, an at rest (or background) EMG signal is generated by the patient 56 and is detected on the active electrodes 52 with respect to the reference electrode 54. An EMG sensing circuit 64 conditions this input signal and converts it into a digital word for processing by software implemented on the personal computer 46 in FIG. 1. The computer software (or the therapist 44) nulls out the background signal generated by the patient. The therapist then asks the patient to attempt to flex his right wrist. This signal is monitored by the therapist on the computer display 60 and the therapist selects a "threshold value" with respect to the wrist movement attempt signal generated by the patient. When the therapist activates a stimulation sequence, a stimulation signal will not actually be generated by the stimulator 40 until the patient generates an EMG signal at or above the threshold level.

After the stimulation sequence has been initiated, and an EMG signal at or above the threshold value has been detected by the software in the computer, the software sends a series of digital stimulation words over a data bus 66 to an electrical stimulation circuit 68 in FIG. 4. The stimulation circuit converts individual stimulation words into a plurality of complex, bipolar voltage pulses forming a series of therapeutic pulse trains defining a stimulation signal which is transferred to a transformer potentiometer 70 visible on a face plate of the stimulator, and available for manipulation by the therapist 44. The potentiometer is preadjusted by the therapist in accordance with the overall amplitude desired and entered by the therapist on the computer screen 60. The output of the potentiometer is then directed through the active electrodes 52 to stimulate the patient. The computer can also control the second channel which has a pair of active electrodes 72 which are triggered either by the threshold EMG signal detected by the EMG sensing circuit 64 of channel one or by direction of the therapist. A separate, second channel transformer potentiometer 74 is provided on the stimulator adjacent to the potentiometer 70 for the first channel.

Figure 6A:
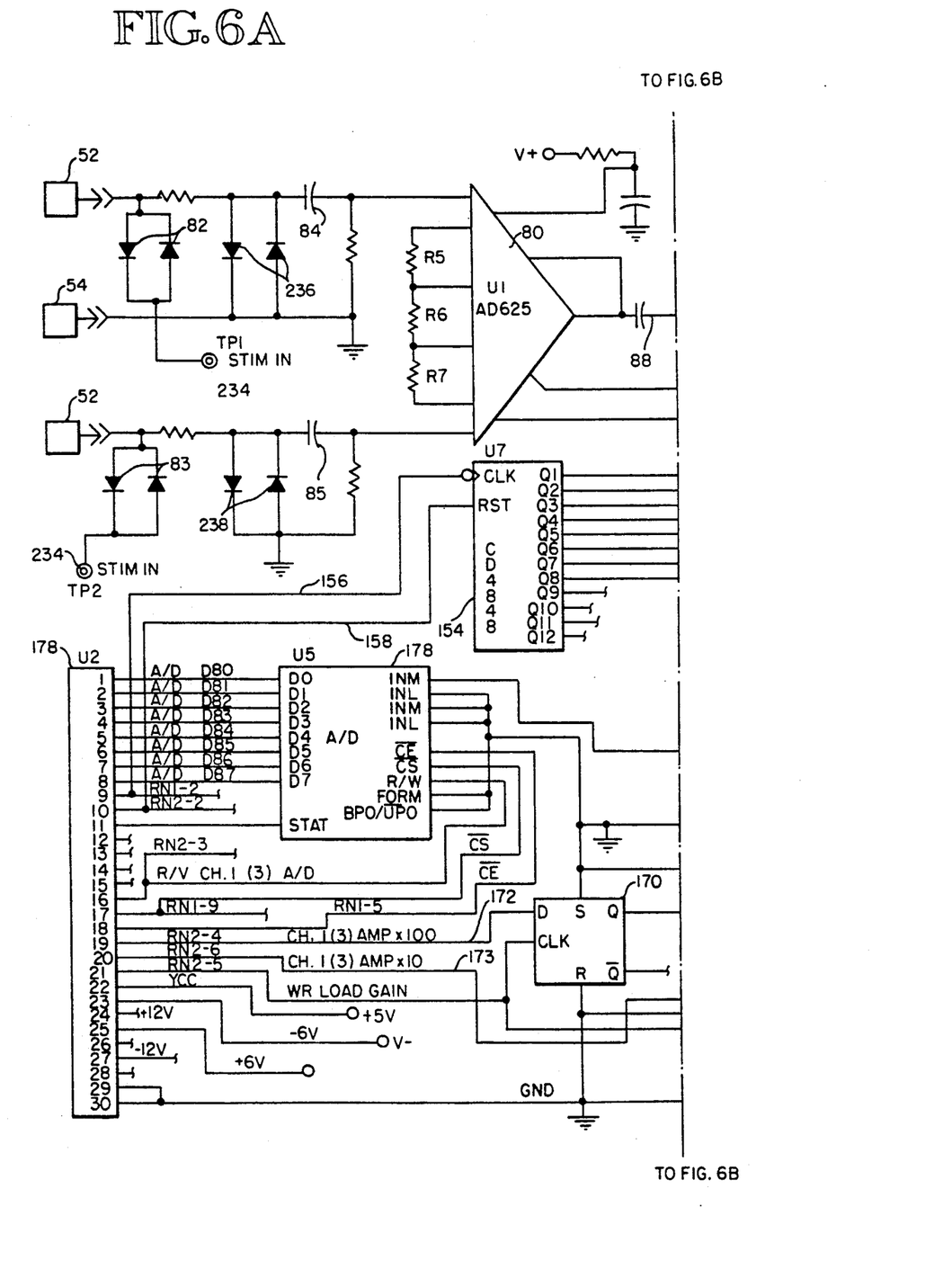
FIGS. 6A and 6B are detailed electronic schematics of an electromyographic sensing circuit shown at reference numeral 64 in FIG. 4.
Figure 6B:
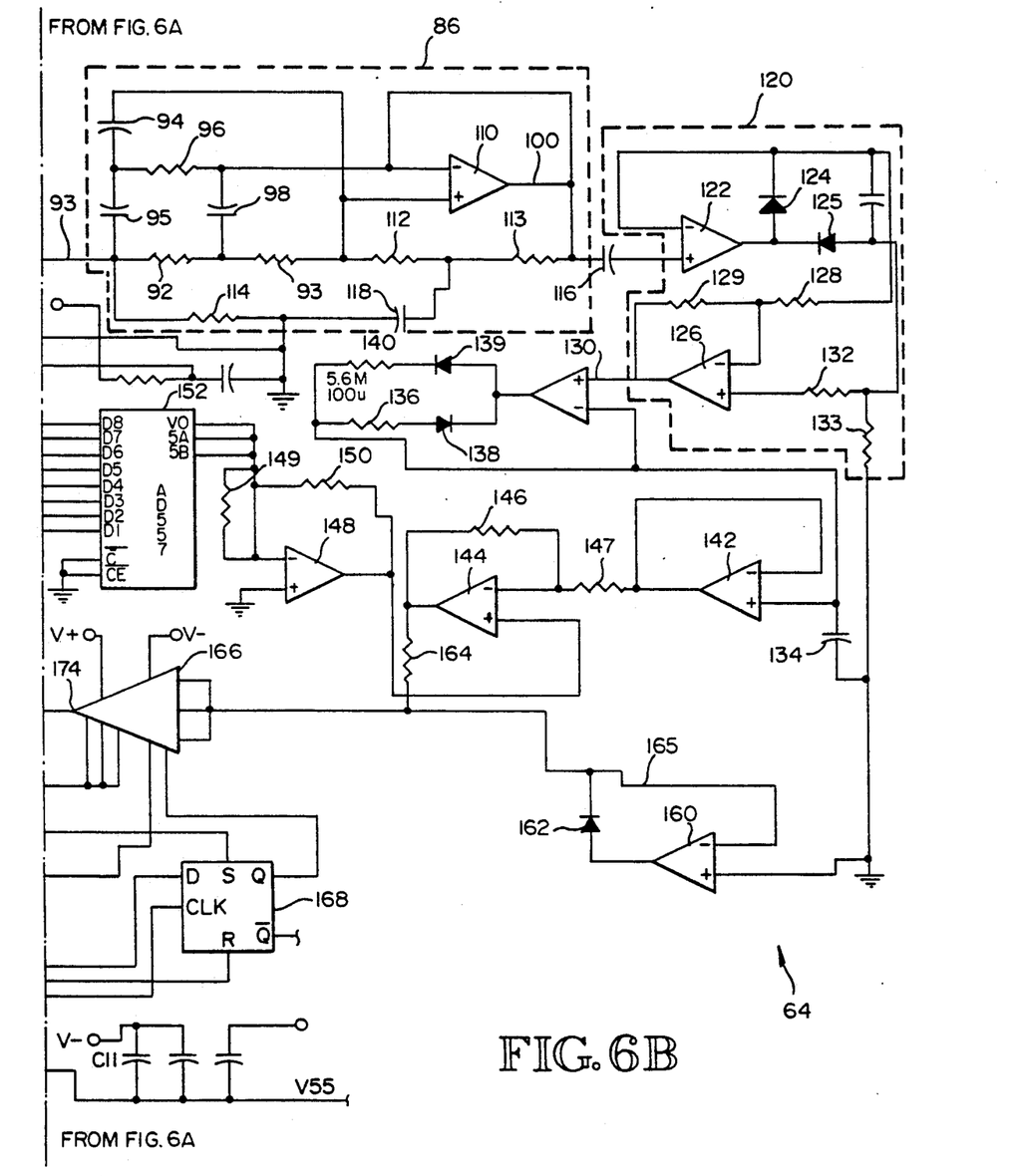

As shown in detail in FIG. 6, the EMG signals from the patient are delivered from the active electrodes 62 to an instrumentation amplifier 80 programmed by appropriate resistor selection to act as a differential amplifier having a gain of 2,500. An appropriate amplifier is a type AD 625. Pairs of limiting diodes 82, 83 prevent the EMG signals from entering the possibly low output impedance of the transformer potentiometer 70 as will be described further hereinbelow. 0.47 $\mu$F and one Meg Ohm capacitor resistor pairs 84, 85 provide the appropriate voltage drop and AC coupling to the amplifier 80. An active twin-T notch filter 86 filters out 60 $H_z$ line frequency from the amplified EMG signal available at the amplifier output 0.01 $\mu$F coupling capacitor 88. Resistors 92 and 93 and capacitors 94, 95 have values of 640K Ohms, and 0.01 $\mu$F respectively. A junction between resistor 96 having a value of 320K Ohms and capacitor 98 having a value of 0.02 $\mu$F is fed by the output 100 of a voltage follower 110 which provides the notch filter 86 with a relatively narrow band width. One Meg Ohm resistors 112, 113 and 114 provide high impedance voltage paths to ground the notch filter 86, voltage follower 110, and the next signal conditioning stage 120 which is AC coupled by a 0.47 $\mu$F capacitor 116 and 0.05 $\mu$F capacitor 118.

The output of capacitor 116 enters a full wave rectifier 120 employing small signal diode design to effectively rectify the 25-250 milli-volt signal entering the non-inverting input of operational amplifier 122. The output of the operational amplifier 122 is connected to a "forward bias" diode 124 and "reverse bias" diode 125.

The forward bias diode 124 forms part of a feedback loop to the inverting input of operational amplifier 122 and to the inverting input of operational amplifier 126 through 20K Ohm input and feedback resistors 128 and 129, respectively. Thus, a positive signal entering the non-inverting input of operational amplifier 122 is directed through the forward bias diode 124 (diode 125 is reverse biased and therefore "open") and is amplified by the closed loop gain (−1) of inverting amplifier 126 producing a negative pulse at the non-inverting input of peak detector circuit 130. It should be remembered that when the forward bias diode 124 is conducting due to a negative cycle having been encountered at the non-inverting input of operation amplifier 122, the reverse bias diode 125 is not conducting causing the non-inverting input of operation amplifier 126 to be connected to ground through 10K Ohm and 2K Ohm 132 and 133 respectively. Conversely, a negative signal received at the non-inverting input of operational amplifier 122 causes the diode 125 to become forward biased drawing current from ground through resistor 133 and through the low output resistance of operational amplifier 122. This causes a negative voltage to be sensed at the non-inverting input of operational amplifier 126 which now behaves as a voltage follower because the diode 124 is reverse biased and does not conduct. Note that resistor 128 is connected to the high input impedance of operational amplifier 122 and thus prevents operation amplifier 126 from acting as a non-inverting amplifier. The closed loop gain of this circuit is positive unity which therefore results in a negative pulse at the non-inverting input of peak detector circuit 130.

Therefore, both positive and negative waves detected by the active electrodes 52 are converted into amplified, 60 $H_z$ filtered an rectified negative pulses at the non-inverting input of peak detector 130. The operational amplifier comprising a peak detector 130 acts as a differential amplifier comparing the charge on a one $\mu$F capacitor 134 to the lumped, negative d.c. signal of the non-inverting input. If the capacitor is not yet charged, the operational amplifier 130 draws current from ground, through the capacitor 134, through the 100K Ohm resistor 136 and into the low output impedance of the operational amplifier 130. Thus, the capacitor charges with a relatively fast time constant of 0.1 seconds. However, once the capacitor is charged (i.e., the potential at the non-inverting input of operational amplifier 130 retreats from its negative maximum back towards ground potential, diode 138 becomes reversed biased while the diode 139 is forward biased and conducts through the 5.6M Ohm resistor 140. The capacitor thus discharges (in the negative sense) through the low output impedance of the peak detector 130, the diode 139, the resistor 140 and ground, with the relatively slow time constant of 5.6 seconds until the voltage on the capacitor 134 is lower in magnitude than the magnitude of the negative signal at the non-inverting input of operational amplifier 130, at which time diode 139 is reversed biased, diode 138 conducts and the capacitor is recharged. Thus, the capacitor 134 substantially measures the peak values of the EMG signals detected by the active electrodes 52 with respect to the reference electrode 54 as a negative, substantially direct current signal. This signal is buffered by an operational amplifier 142 configured as a voltage follower whose output is directed to the inverting input of an operational amplifier 144 configured as a differential amplifier having a feedback resistor 146 and a source resistor 147 both having values of 20K Ohms.

The non-inverting input of differential amplifier 144 receives a nulling signal by way of an operational amplifier 148 having feedback and source resistors 149, 150 each having a value of 10 Ohms, thus configuring this operational amplifier 148 as an invertor with a voltage gain of −1. The invertor receives an analog signal from a conventional digital-to-analog converter 152 which is driven by a conventional 8-bit counter 154. As will be explained further hereinbelow, the software in the computer 46 is continuously monitoring the EMG output of the active electrode 52 during a nulling step. During this nulling step, the computer initiates the counter 154 with clock pulses generating an increasing, analog output from digital-to-analog converter 152 which is inverted and applied to the non-inverting input of differential amplifier 144. When the negative signals at the inverting and non-inverting inputs are equal, the computer 60 determines that the background EMG signal detected by the active electrodes 52 has been nulled and the computer stops generating clock pulses on line 156. This count is held and therefore the output of differential amplifier 144 nulled until a reset signal is sent on line 158.

Operational amplifier 160 is configured by diode 162 to clamp the output of the differential amplifier 144 at 20K Ohm resistor 164 to ground. That is, the output of differential amplifier 144 cannot fall below zero. It should be remembered that the diodes 124, 125, 138, 139 and 162 are acting as small signal diodes because they are connected directly to the outputs of their respective operational amplifiers. This enables these diodes to follow very small signals at the input to the operational amplifiers. When the diodes are not fully biased, these operational amplifiers are temporarily operating under open loop condition. Thus, if there is even a minute difference between the voltage at the non-inverting input and the diode terminal which is not connected to the immediate output of the operational amplifier, the operational amplifier strongly drives its output in the polarity of the input signal until the diode is forward biased. In the case of diode 162, the voltage of the output of resistor 164 is positive with respect to the non-inverting input of operational amplifier 160 (i.e., positive with respect to ground). The operational amplifier quickly drives the diode into reverse bias which opens the feedback loop 165 and causes the voltage of the non-inverting input of operational amplifier 160 to float. However, if the output of resistor 164 is less than ground the immediate output of the operational amplifier 160 is strongly positive and thus forwardly biases the diode 162 and closes the feedback loop and clamping the output of resistor 164 to ground. This action prevents the computer for any reason from "over nulling" operational amplifier 144. Thus, the output of resistor 164 cannot go below ground.

The output of resistor 164 is directed to a conventional, programmable operational amplifier 166 such as a PGA 102 type integrated circuit which is controlled by two D-type flipflops 168, 170. The D input of each flipflop is controlled by the computer from lines 172, 173. The set and reset terminals of these flipflops are grounded. The gain of programmable amplifier 166 is either unity, 10 or 100 and thus provides the scale function as will be described further hereinbelow for graphical representation of EMG signals on the computer display 60. The output 174 of the programmable amplifier 166 is directed to the input of a conventional 8-bit analog-to-digital converter 178 such as a type AD 670 converter. This converter converts the analog signal to an 8-bit word which is then output to the computer 46 by way of a connector terminal 178.

Viewing the EMG signals generated by the patient enables the therapist 44 to determine what threshold level should be set for triggering an automatic stimulation signal selected by the therapist.

Stimulation signals

Figure 5:
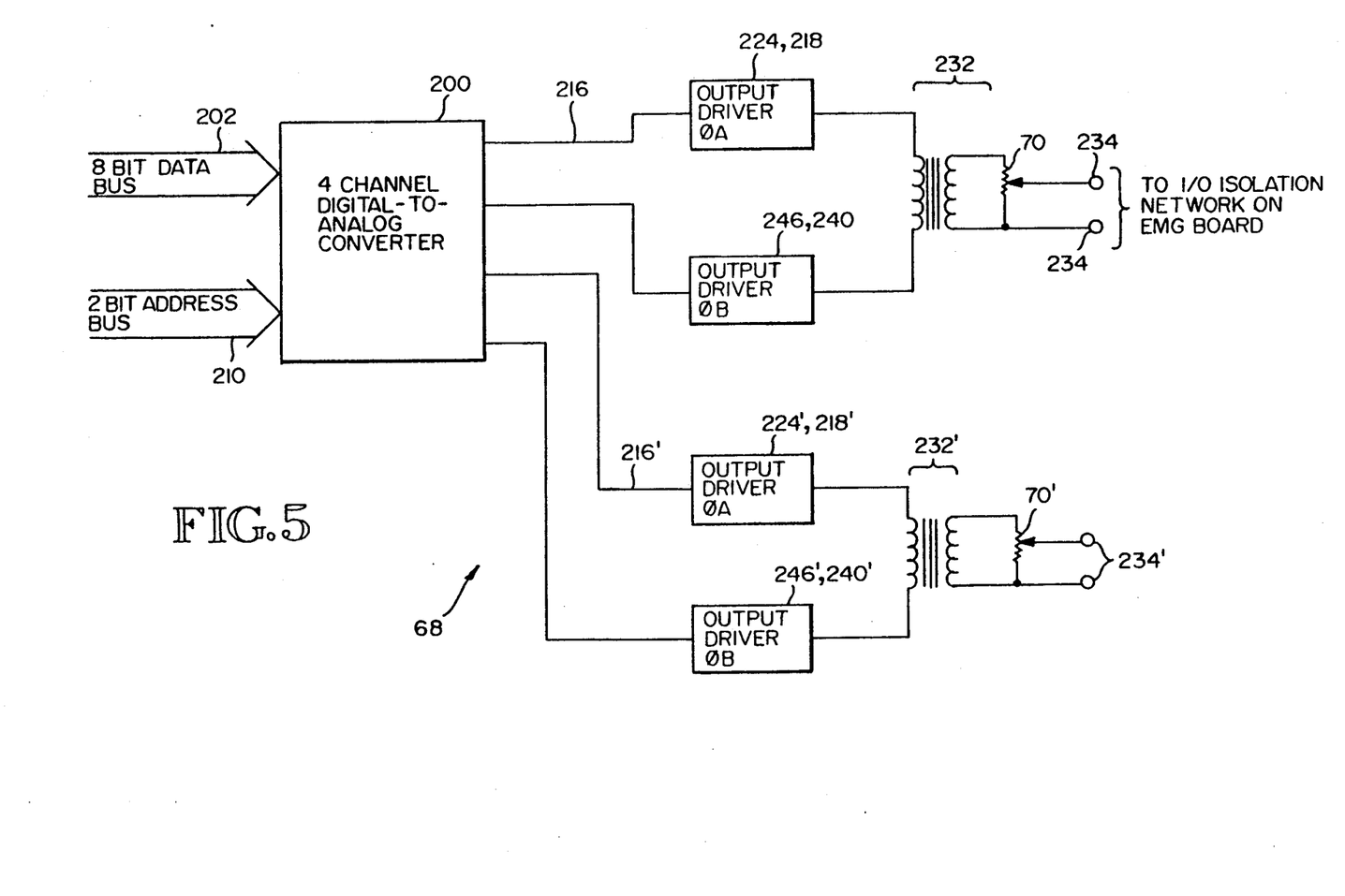
FIG. 5 is a low level block diagram of an electrical stimulation circuit employed by the present invention.
Figure 7A:
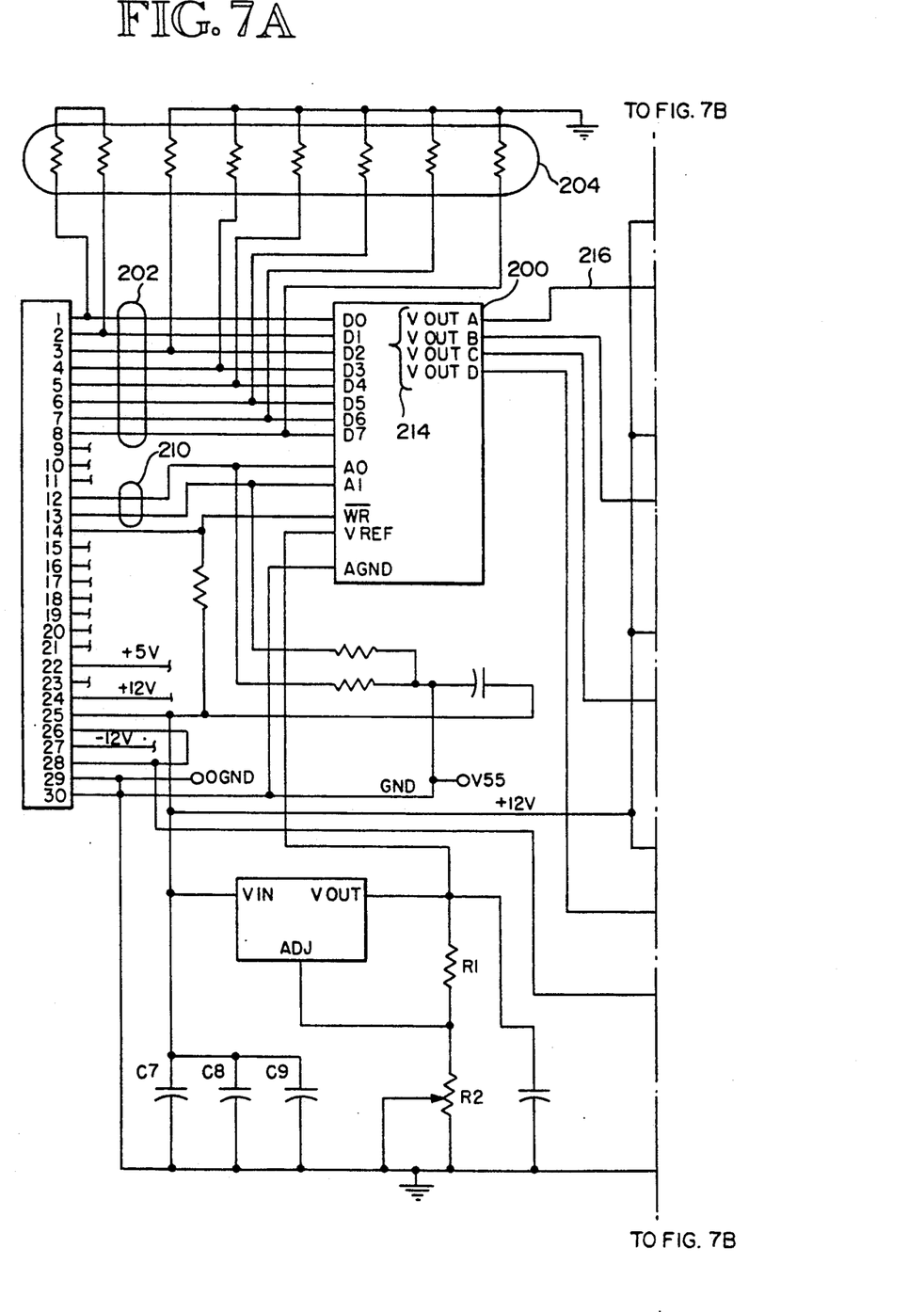
FIGS. 7A and 7B are detailed electronic schematics of an electrical stimulation circuit shown in block form in FIG. 5 and at reference numeral 68 in FIG. 4.
Figure 7B:
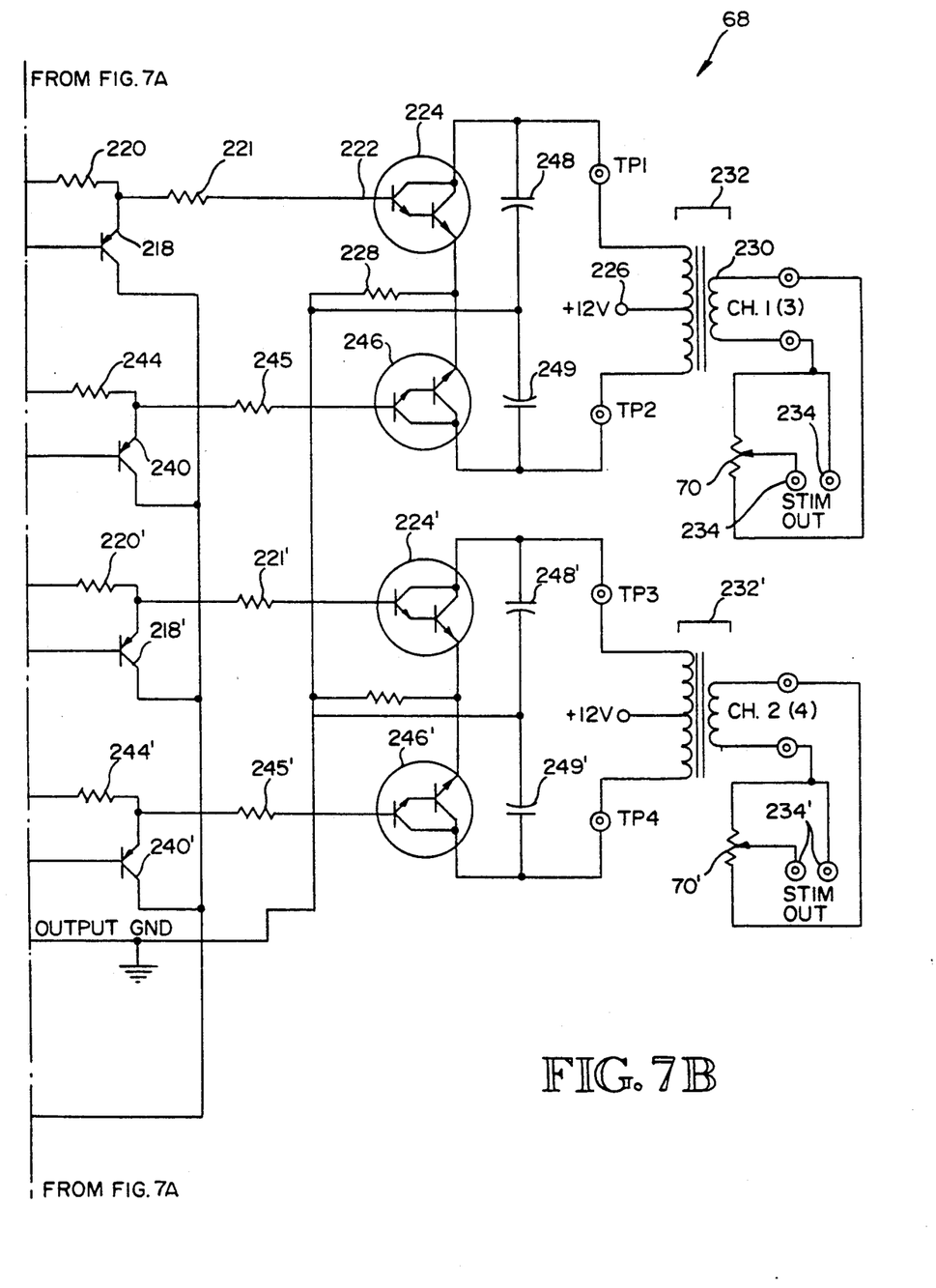

As previously stated and as shown in FIG. 4, once an appropriate stimulation signal has been selected by the therapist, and a suitable EMG trigger has been generated by the patient and received by the sensing circuit 64, electrical stimulation circuits 68 convert digital stimulation words generated by the computer software into a plurality of complex, bipolar voltage pulses whose amplitude is controlled by the potentiometer 70 on the face of the stimulator 40. FIG. 7 is a detailed circuit diagram of the stimulation circuit 68. Eight-bit stimulation words are delivered to a quad digital-to-analog converter 200 such as an AD 7226 type converter by way of data lines 202. Resistor network 204 consisting of eight 20K Ohm resistors provide voltage pulldown in case of open data lines. Two address lines 210 determine which one of four internal digital-to-analog converters 214 will be associated with each 8-bit word. Address zero will select converter A on line 216 which energizes conventional PNP transistor 218 through 2K and 100 Ohm bias resistors 220 and 221 respectively. The transistor 218 thus biases the base 222 of a Darlington pair 224 causing current to flow from the center tap of a step-up transformer through a 1 Ohm, 3W resistor 228 to ground. This generates an amplified voltage pulse in the secondary winding 230 of transformer 232. The final magnitude of the pulse delivered to the stimulation outputs 234 of channel one is regulated by potentiometer 70 on the face of the EMG stimulator 40. Note that the output 234 is directed into the electrical stimulation circuit 68 in FIG. 6 near the input to the instrumentation amplifier 80. In order to avoid overloading the inputs of this amplifier, pairs of clamping diodes 236, 238 limit the voltage potential of each input to amplifier 80 to the forward bias voltage of each diode regardless of the stimulation voltage which may be up to 100 volts. In this technique, the same active electrodes are used for both EMG detection and delivery of stimulation signals. FIG. 5 is a high level block diagram of stimulation circuit 68 showing channels one and two.

Returning to FIG. 7, (and remembering that we have just delivered a positive pulse to the active electrodes by way of digital-to-analog converter A of quad converter 200), we are now prepared to deliver the polar (or negative) pulse by addressing digital-to-analog converter B of quad converter 214. The 8-bit word delivered over lines 202 are now routed to PNP transistor 240 biased by resistors 244, 245 as described above with respect to transistor 218. Transistor 240 activates Darlington pair 246. Current flows from the center tap 226 through the Darlington pair 246, resistor 228 to ground generating a negative pulse in secondary winding 230 which is delivered to the active electrodes. A pair of ten $\mu$F capacitors 248 and 249 slightly dampen the output signals. The component values and operation of channel two in FIG. 7 is identical to that described for channel one. It is to be noted here that the positive and negative pulse of each bipolar cycle is independently controlled by the addressable selection of the appropriate digital-to-analog converter 214, and the 8-bit digital simulation word appearing on line 202. Thus, as shown in FIG. 2, it is possible to generate a positive square wave type pulse followed by an exponentially decaying negative pulse (exponential pulses are modeled by a sequence of small square pulses each decreasing in magnitude so as to generate the desired RC time constant). As will be appreciated by those of ordinary skill in the art, by employing thoroughly digital control over the pulse shape and duration there are no mechanical constraints limiting the stimulating signal which can be generated by the system other than the total amplitude which is limited by the turns ratio of step up transformer 232 and the value of the power supply at the center tab 226. It is a trivial exercise to modify the pulse shape to any desired configuration.

Interactive Graphic Interface

Figure 8:
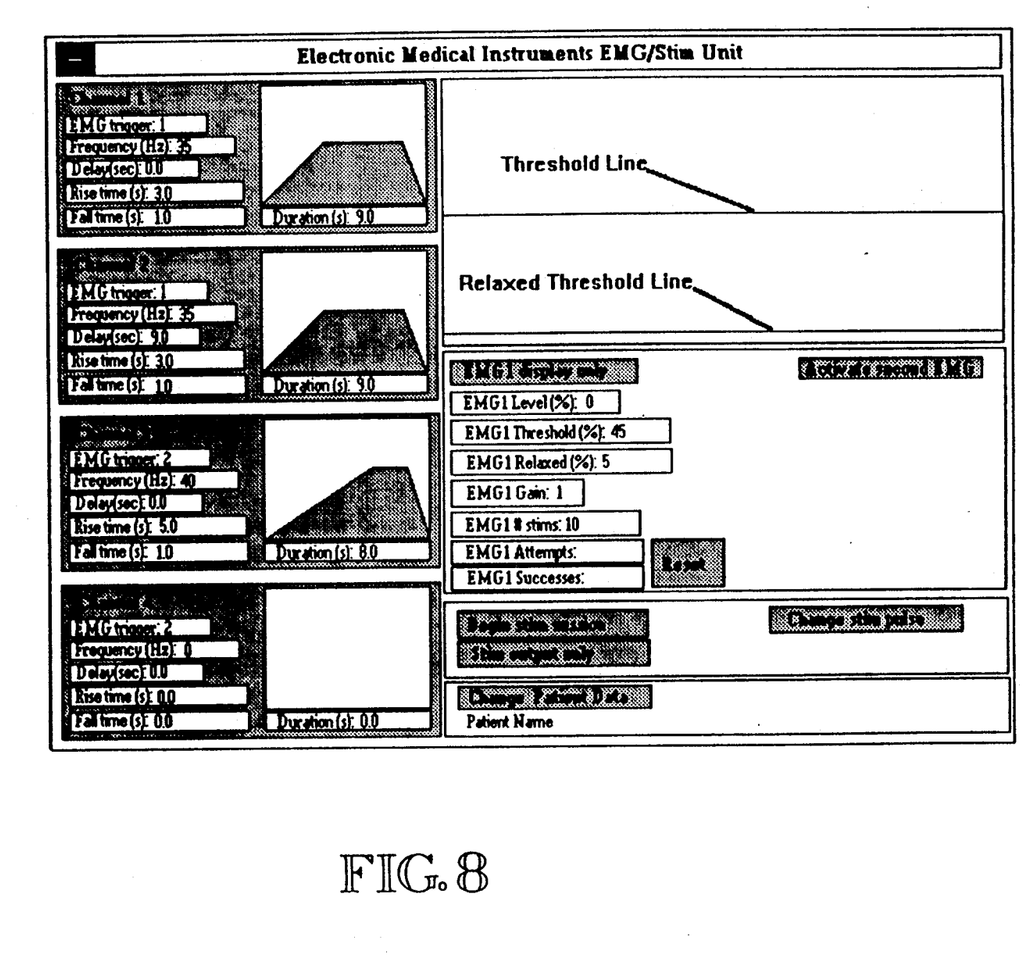
FIG. 8 is a representation of a graphical interface between the therapist and the stimulation and sensing circuits and is generated by a computer program of the present invention.

FIG. 8 illustrates an interactive graphic interface generated by computer software stored in the personal computer 46. The interface is of the "windows type" which can be accessed and manipulated by a pointing device such as the mouse or track ball 58 in FIG. 1. On the left side of the interface, the software presents graphical information related to each of the four channels. In the upper right hand corner of the interface, a simulated screen illustrates the relaxed EMG threshold 250 generated by the therapist at 5% of full scale and an EMG threshold line 252 at 45% of full scale set by the therapist. If asked to attempt a muscle contraction, the patient might generate a wave form looking like trace 254. The trace will move to the right and trail off to the left with time as on an electrocardiogram. By clicking on the "EMG 1 threshold (%) box", the therapist can raise or lower the upper threshold line in accordance with the EMG attempts 254 generated by the patient. The lower threshold line can be adjusted upwardly for patients, such as children who have difficulty reaching a relaxed state after a muscle contraction. When in automatic mode, a patent's EMG must exceed the upper threshold 252 to initiate a stimulation series. The patient's EMG must then fall below the relaxed threshold 250 and rise above the upper threshold 252 again before a second stimulation in the series will be initiated.

The window 258 in the center right hand side of the display has control boxes which in order from top to bottom: display the real time EMG level (in percent of full scale) generated by the patient; the EMG threshold (in percent of full scale) selected by the therapist; the relaxed EMG threshold; the gain of programmable operational amplifier 166 (1, 10 or 100); the number of EMG stimulations selected (a stimulation is defined to be a single pulse train here); the number of EMG attempts by the patient; and, the number of EMG attempts which exceeded the threshold line (successes). The channel boxes on the left hand side of the display identify which trigger (if any) that particular channel will use, the frequency of the pulses, the delay (if any) after which each pulse train will begin on this channel, the rise time 16, the fall time 28, the normalized amplitude 18 and the duration of the pulse train (see also FIG. 2). As each of these parameters is adjusted, the size and shape of the pulse train envelope changes. Note that any channel can be triggered by either channel one or three due to the data bus structure 66 of FIG. 4.

Figure 9:
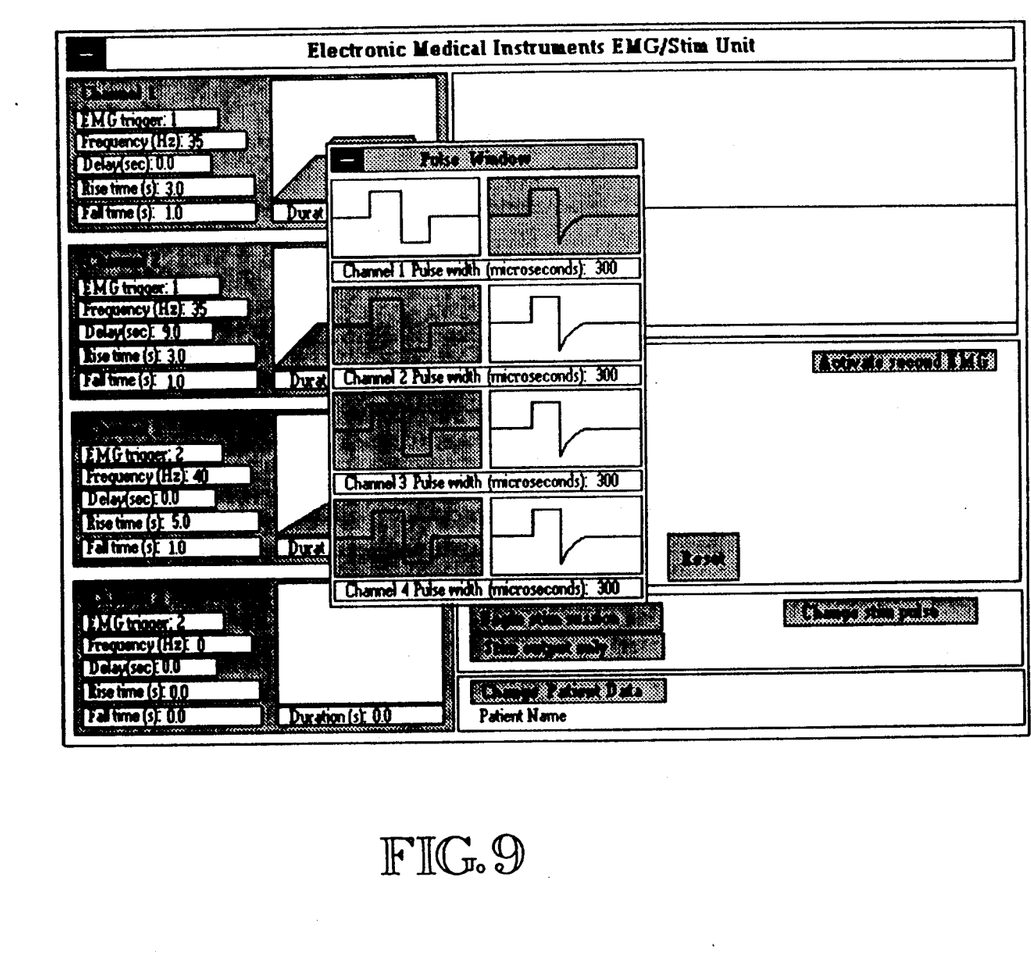
FIG. 9 is a window illustrating different pulse shapes employed by the present invention.
Figure 10:
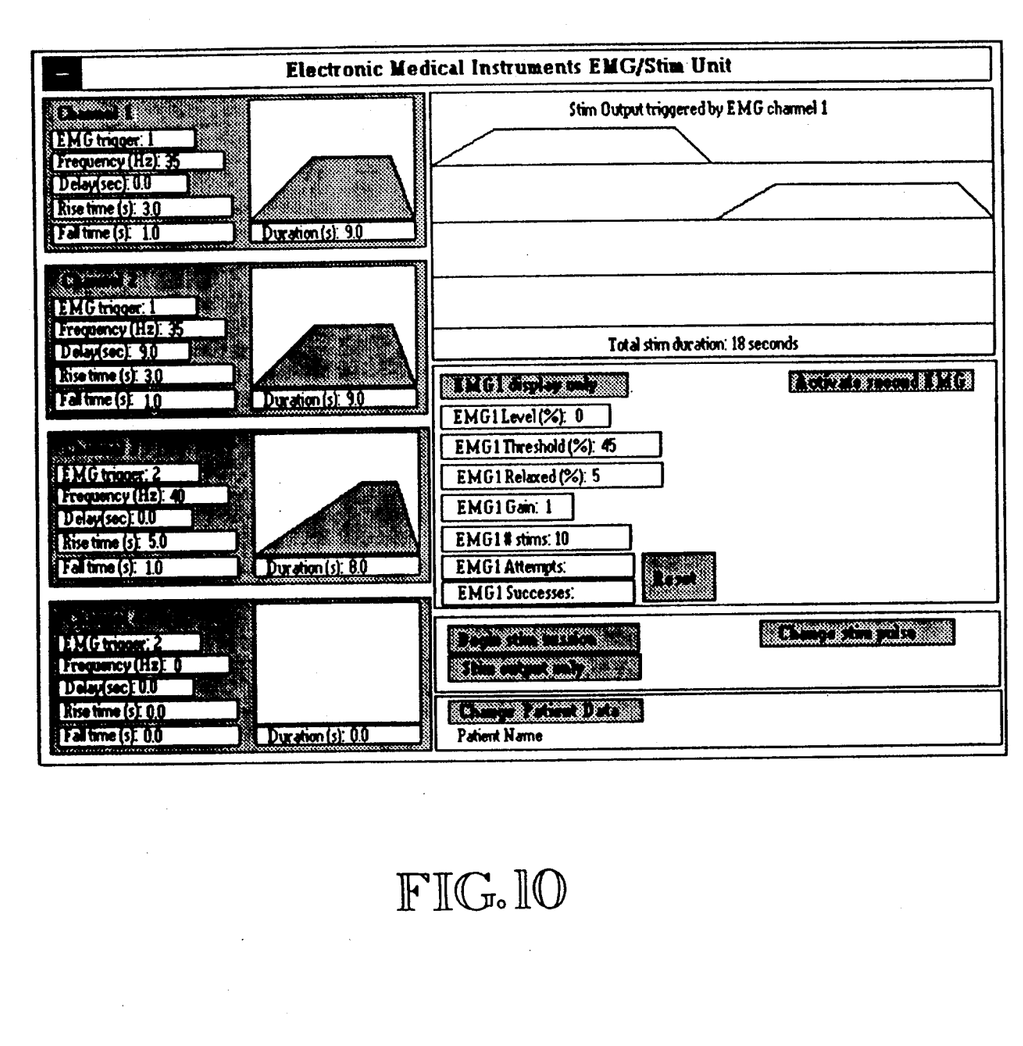
FIG. 10 is an illustration of a graphic display showing a plurality of pulse trains defining a stimulation signal graphically displayed by the computer program of the invention.

The therapist can therefore readily create a custom tailored stimulation signal without having to perform mathematical calculations or mental two dimensional visualization. Different pulse train envelopes are shown for channels 2 and 3; in this example channel 4 is unused. As shown in FIG. 10, the window in the upper right hand corner of the screen previews an entire stimulation signal before stimulations are initiated. To initiate a stimulation session, the appropriate box is clicked on above the patient data box. As shown in FIG. 9, an additional window can be opened (in this example the scale window) allowing a variety of different pulse shapes for each channel, each with predefined or preselected pulse widths. Additional windows (not shown) can be selected which change the time constant of exponential decay, duty cycle, etc.

Finally, the box at the lower right hand corner of the display opens another box containing data with respect to the patient including name, address, etc.

Figure 11:
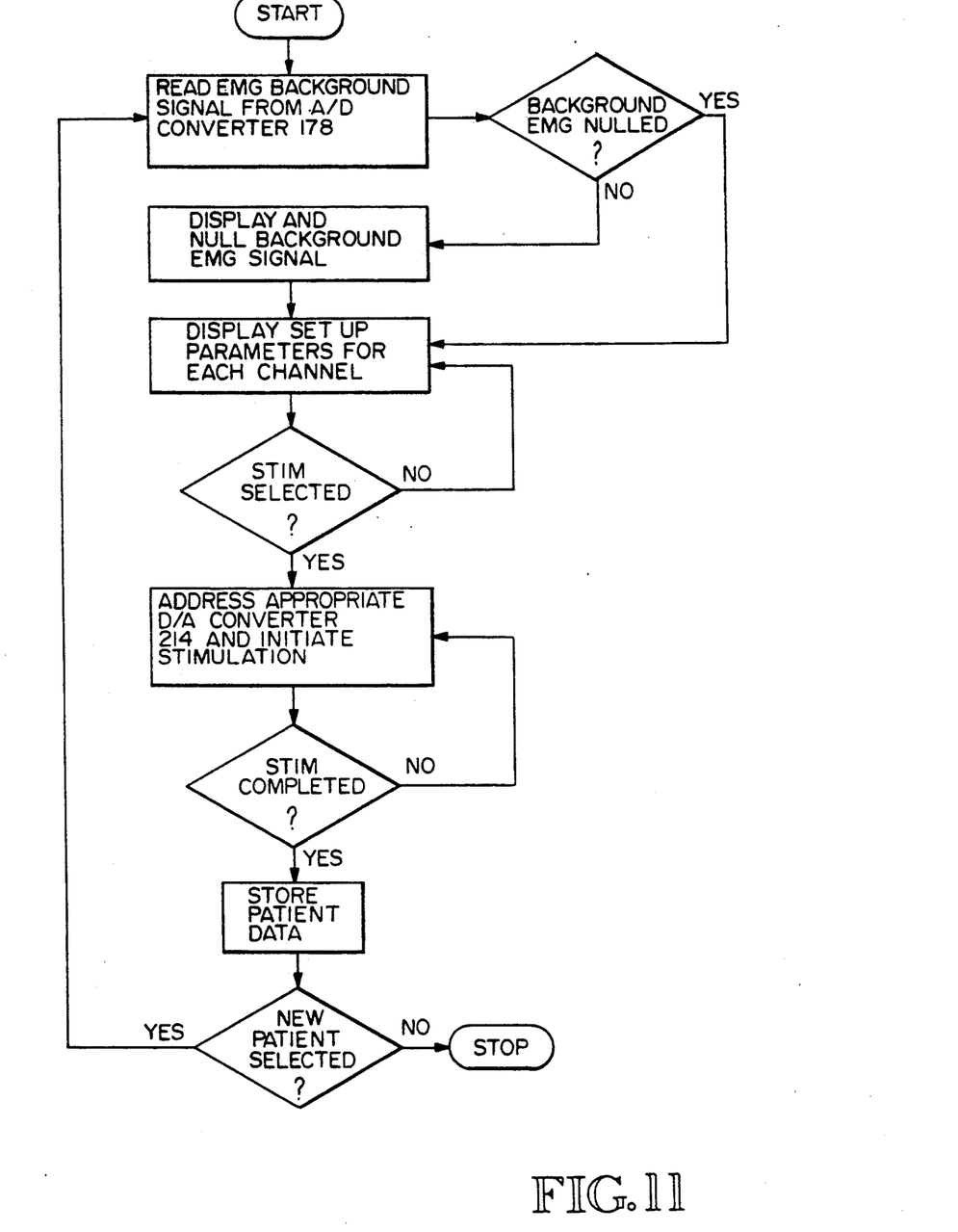
FIG. 11 is a flow chart illustrating the logic of flow of the computer program employed by the present invention.

FIG. 11 illustrates the logic flow executed by the computer program of the present invention. In the beginning of a session, the EMG background signal is read from the A to D converter 178. If the background EMG signal has not been nulled, the background signal is displayed and nulled on the computer display. Once the background EMG signal has been nulled, the display allows the therapist to set up various parameters for each channel. Once the perimeters have been selected to the therapist's satisfaction, and the sequence of pulse trains visually has been previewed, the therapist may proceed with a stimulation session, either initiated by the patient or by the therapist. The appropriate digital to analog converter 214 in FIG. 7 is selected to generate the appropriate pulse trains. The therapist monitors the session on the computer display. Once the stimulation session is completed to the satisfaction of the software, or the therapist, the stimulation session is terminated, the patient data recorded, and a new patient record can be selected.

Upon reviewing this disclosure, those of ordinary skill in the art will appreciate various other embodiments which fall within the scope of the above description. Therefore the scope of this invention is not to be limited by the above description, but is to be determined by the claims which follow.

We claim:

1. An electromyographic treatment system having a treatment device and including and operated by a computer having an interactive graphic display, the treatment device comprising:

a reference electrode and a pair of active electrodes for sensing electromyographic signals from a patient and for delivering an electrical stimulation signal to the patient;

an electromyographic sensing circuit connected to the electrodes, having input signal conditioning means for converting the sensed signals to digital electromyographic words representative of the sensed signals and having an automatic nulling means for establishing a null signal level representative of a background electromyographic signal generated by the patient at rest;

an electrical stimulation circuit connected to the active electrodes, having output signal conditioning means for converting a series of digital stimulation words into a plurality of complex, bipolar voltage pulses forming a series of preselected therapeutic pulse trains defining a stimulation signal;

electronic interconnecting means for interconnecting the sensing and stimulation circuits and for interconnecting the sensing and stimulation circuits with the computer; and software means for use in conjunction with the personal computer for accepting the electromyographic words and generating a normalized image of the sensed signals for display on the interactive graphical display, enabling a therapist to view the sensed signals, enter a plurality of therapeutic parameters into the display, view a graphic representation of a resulting therapeutic pulse train, and for sending digital stimulation words representative of the therapeutic parameters to the stimulation circuit.

2. The treatment device of claim 1, wherein the software means includes selected display parameters for: pulse train repetitions, rise time, amplitude, fall time and duration; pulse cycle frequency and shape; electromyographic threshold for stimulation; and, wherein the software means also stores the selected display parameters for different patients and generates a normalized real time graph of the stimulation signal.

3. The treatment device of claim 1, including a plurality of reference electrodes and active electrode pairs connected to additional sensing and stimulation means connected to the interconnecting means, wherein the software means display parameters include delay times for each active electrode pair.

4. The treatment device of claim 1, wherein the stimulation circuit has two addressable digital to analog converters for generating addressed unipolar pulses from the digital stimulation words and wherein the device further includes a center tapped voltage transformer having opposite sides of a primary winding connected to the two addressable digital to analog converters so that the addressed unipolar pulses are directed to opposite sides of the center taped voltage transformer to produce the bipolar voltage pulses.

5. The treatment device of claim 1, wherein the sensing circuit includes in series a precision amplifier, a 60 Hz filter, a full wave rectifier generating negative pulses, a peak detector, an automatic offset nulling circuit having an output, a scale amplifier having digitally selectable gain, and an analog to digital converter.

6. The treatment device of claim 5, including clamp circuit means connected to the output of the offset nulling circuit for preventing the output from falling below a ground voltage thereby preventing overnulling.

7. The treatment device of claim 5, wherein the full wave rectifier includes a voltage follower having an output and having inverting and non-inverting inputs with a first forward biased diode connected between the output and the inverting input of the follower as part of a negative feedback loop and to an inverting input of an operational amplifier configured with first and second resistors as an inverting amplifier having a voltage gain of $-1$, the follower output also being connected by a second reverse bias diode to a grounded third resistor and through a fourth resistor to a non-inverting input of the operational amplifier now configured as a non-inverting amplifier with a voltage gain of $+1$ due to the opposite biasing of the first and second diodes.

8. An electromyographic treatment system having a treatment device and including and operated by a computer having an interactive graphic display, the treatment device comprising:

a reference electrode and a pair of active electrodes for sensing electromyographic signals from a patient and for delivering an electrical stimulation signal to the patient;

an electromyographic sensing circuit connected to the electrodes, having input signal conditioning means for converting the sensed signals to digital electromyographic words representative of the sensed signals;

an electrical stimulation circuit connected to the active electrodes, having output signal means for converting a series of digital stimulation words into a plurality of complex, bipolar pulses forming a series of preselected therapeutic pulse trains defining a stimulation signal;

electronic interconnecting means for interconnecting the sensing and stimulation circuits and for interconnecting the sensing and stimulation circuits with the computer; and software means for use in conjunction with the personal computer for accepting the electromyographic words and generating a normalized image of the sensed signals for display on the interactive graphical display, enabling a therapist to view the sensed signals, enter a plurality of therapeutic parameters into the display, view a graphic representation of a resulting therapeutic pulse train, and for sending digital stimulation words representative of the therapeutic parameters to the stimulation circuit.

9. The treatment device of claim 8, wherein the software means includes selected display parameters for: pulse train repetitions, rise time, amplitude, fall time and duration; pulse cycle frequency and shape; electromyographic threshold for stimulation; and, wherein the software means also stores the selected display parameters for different patients and generates a normalized real time graph of the stimulation signal.

10. The treatment device of claim 8, including a plurality of reference electrodes and active electrode pairs connected to additional sensing and stimulation circuits connected to the interconnecting device, wherein the software means display parameters include delay times for each active electrode pair.

11. The treatment device of claim 8, wherein the stimulation circuit has two addressable digital to analog converters for generating addressed unipolar pulses from the digital stimulation words and wherein the device further includes a center tapped voltage transformer having opposite sides of a primary winding connected to the two addressable digital to analog converters so that addressed unipolar pulses are directed to opposite sides of the center taped voltage transformer to produce the bipolar voltage pulses.

12. The treatment device of claim 8, wherein the sensing circuit includes in series an instrumentation amplifier, a 60 Hz filter, a full wave rectifier generating negative pulses, a peak detector, an automatic nulling device establishing a null signal level representative of a background electromyographic signal generated by the patient at rest, a scale amplifier having digitally selectable gain, and an analog to digital converter.

13. The treatment device of claim 8, including a clamp circuit and an automatic nulling device having an output, wherein the automatic nulling device output is connected to the clamp circuit so as to prevent the output from falling below a ground voltage thereby preventing overnulling which can be uncomfortable to the patient.

14. The treatment device of claim 13, wherein the full wave rectifier includes a voltage follower having an output and having inverting and non-inverting inputs with a first forward biased diode connected between the output and the inverting input of the follower as part of a negative feedback loop and to an inverting input of an operational amplifier configured with first and second resistors as an inverting amplifier having a voltage gain of $-1$, the follower output also being connected by a second reverse bias diode to a grounded third resistor and through a fourth resistor to a non-inverting input of the operational amplifier now configured as a non-inverting amplifier with a voltage gain of $+1$ due to the opposite biasing of the first and second diodes.

15. A method for generating complex bipolar pulses forming a series of preselected therapeutic pulse trains defining a stimulation signal, comprising the steps of:

viewing an electromyographic background signal from a patient at rest on a screen in a time domain;

enabling a digital counter which drives a digital to analog converter until the background signal is nulled out;

asking the patient to initiate a contraction of a muscle of interest so as to generate an electromyographic signal;

viewing a representation of the electromyographic signal and entering a threshold electromyographic level into a graphic interface in response thereto;

entering a plurality of therapeutic parameters into the graphic interface, the parameters being represented as digital words in a computer program; and converting the digital words into stimulation signals and applying the stimulation signals to a patient.

16. The method of claim 15, wherein during the threshold entering step both upper and relaxed threshold electromyographic levels are entered into the graphic interface.

* * * * *